United States Patent
Wu

(10) Patent No.: US 8,016,758 B2
(45) Date of Patent: Sep. 13, 2011

(54) USER INTERFACE FOR MEDICAL IMAGING INCLUDING IMPROVED PAN-ZOOM CONTROL

(75) Inventor: Tony Wu, San Jose, CA (US)

(73) Assignee: SonoWise, Inc., San Jose, CA (US)

( * ) Notice: Subject to any disclaimer, the term of this patent is extended or adjusted under 35 U.S.C. 154(b) by 1693 days.

(21) Appl. No.: 11/222,059

(22) Filed: Sep. 8, 2005

(65) Prior Publication Data

US 2006/0111634 A1    May 25, 2006

Related U.S. Application Data

(60) Provisional application No. 60/623,616, filed on Oct. 30, 2004.

(51) Int. Cl.
  *A61B 8/00* (2006.01)
  *G06F 3/05* (2006.01)
(52) U.S. Cl. .......... 600/440; 600/437; 715/719
(58) Field of Classification Search ........... 600/437, 600/459; 345/156; 715/719–723
  See application file for complete search history.

(56) References Cited

U.S. PATENT DOCUMENTS

| | | | |
|---|---|---|---|
| 4,338,948 A | 7/1982 | Perez-Mendez et al. | |
| 4,455,872 A | 6/1984 | Kossoff et al. | |
| 5,052,394 A | 10/1991 | Carpenter et al. | |
| 5,181,778 A | 1/1993 | Beller | |
| 5,289,168 A * | 2/1994 | Freeman | 345/672 |
| 5,339,282 A | 8/1994 | Kuhn et al. | |
| 5,435,312 A | 7/1995 | Spivey et al. | |
| 5,437,281 A | 8/1995 | Lin et al. | |
| 5,549,638 A | 8/1996 | Burdette | |
| 5,551,432 A | 9/1996 | Iezzi | |
| 5,664,573 A | 9/1997 | Shmulewitz | |
| 5,713,356 A | 2/1998 | Kruger | |
| 6,023,632 A | 2/2000 | Wilk | |
| 6,080,108 A | 6/2000 | Dunham | |
| 6,108,439 A | 8/2000 | Ishiguro | |
| 6,117,080 A | 9/2000 | Schwartz | |
| 6,190,915 B1 | 2/2001 | Madsen et al. | |

(Continued)

FOREIGN PATENT DOCUMENTS

EP    1557125    7/2005

(Continued)

OTHER PUBLICATIONS

Speed of sound, [online] [retrieved on Sep. 23, 2005]. Retrieved from the Internet <URL: http://www.amershamhealth.com/medcyclopaedia/medical/Volume%20I/SPEED%200F%20SOUND>.

*Primary Examiner* — Long V. Le
*Assistant Examiner* — Helene Bor
(74) *Attorney, Agent, or Firm* — K&L Gates LLP

(57) ABSTRACT

An ultrasonic image scanning system for scanning an organic object that includes a display system for displaying a scanned image of the organic object in a plurality of display modes wherein the display system further includes a user input device sensor for sensing a motion of a user input device in at least one of display modes to automatically switch from one display mode to a different display mode. Furthermore, the display system further counts a length of time the user input device staying idle in at least one of the display modes for switching the display mode back to a last display mode at a predefined idle time limit.

22 Claims, 4 Drawing Sheets

Cross section A-A'

B and M mode on the same screen

Time

U.S. PATENT DOCUMENTS

| | | |
|---|---|---|
| 6,248,071 B1 | 6/2001 | Lin |
| 6,285,904 B1 | 9/2001 | Weber et al. |
| 6,287,259 B1 | 9/2001 | Grunwald |
| 6,322,511 B1 | 11/2001 | Guracar et al. |
| 6,338,716 B1 | 1/2002 | Hossack et al. |
| 6,540,681 B1 | 4/2003 | Cheng et al. |
| 6,547,730 B1 | 4/2003 | Lin et al. |
| 6,701,341 B1 | 3/2004 | Wu et al. |
| 6,780,153 B2 | 8/2004 | Angelsen et al. |
| 6,783,497 B2 | 8/2004 | Grenon et al. |
| 6,824,514 B2 | 11/2004 | Poland et al. |
| 6,839,762 B1 | 1/2005 | Yu et al. |
| 6,926,672 B2 | 8/2005 | Moore et al. |
| 6,969,352 B2 | 11/2005 | Chiang et al. |
| 7,266,407 B2 | 9/2007 | Li et al. |
| 7,366,995 B2 * | 4/2008 | Montague .................... 715/798 |
| 2001/0027278 A1 | 10/2001 | Kaufman et al. |
| 2003/0001863 A1 * | 1/2003 | Davidson et al. ............. 345/619 |
| 2003/0125625 A1 | 7/2003 | Kelly et al. |
| 2003/0199765 A1 | 10/2003 | Stetten et al. |
| 2004/0006272 A1 | 1/2004 | Vortman et al. |
| 2004/0059221 A1 | 3/2004 | Azuma et al. |
| 2004/0111028 A1 * | 6/2004 | Abe et al. .................... 600/437 |
| 2005/0148899 A1 | 7/2005 | Walker et al. |
| 2005/0251042 A1 | 11/2005 | Sandrin et al. |
| 2005/0256406 A1 | 11/2005 | Barthe et al. |
| 2006/0094959 A1 | 5/2006 | Lin et al. |
| 2006/0094960 A1 | 5/2006 | Phung |
| 2006/0111634 A1 | 5/2006 | Wu |
| 2007/0083110 A1 | 4/2007 | Lin et al. |
| 2007/0276246 A1 | 11/2007 | Lin |
| 2008/0119735 A1 | 5/2008 | Lin et al. |

FOREIGN PATENT DOCUMENTS

| | | |
|---|---|---|
| WO | 2004/041092 | 5/2004 |

* cited by examiner

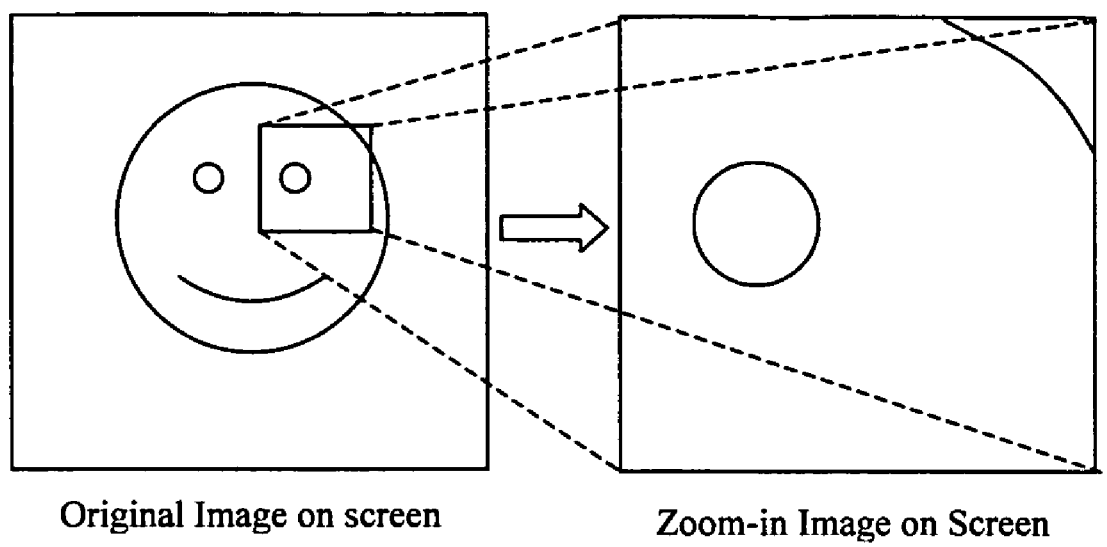
Fig 1. Pan Zoom control

Fig 2A. User has the original image on the screen:

Fig 2B. User pressing Zoom key to bring out the ZROI graphic box:
The user can pan the ZROI with track ball anywhere
on the display.

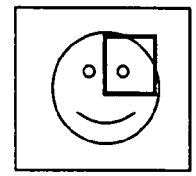

Fig 2C. Press Zoom key another time will display Zoom Window

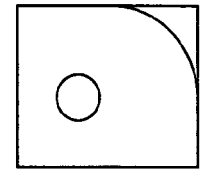

Fig 2D. Touch Trackball for panning will cause the screen to go back
to the original display automatically.

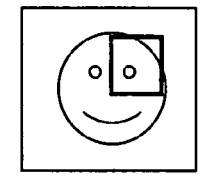

Fig 2E. The user can pan the ZROI to a new location with trackball

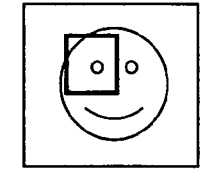

Fig 2F. The screen goes back to the Zoom window when ZROI stays
at the same location (i.e., if trackball is stationary) for a certain
time (e.g. 0.3 second).

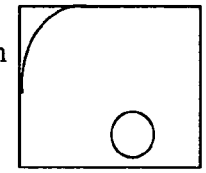

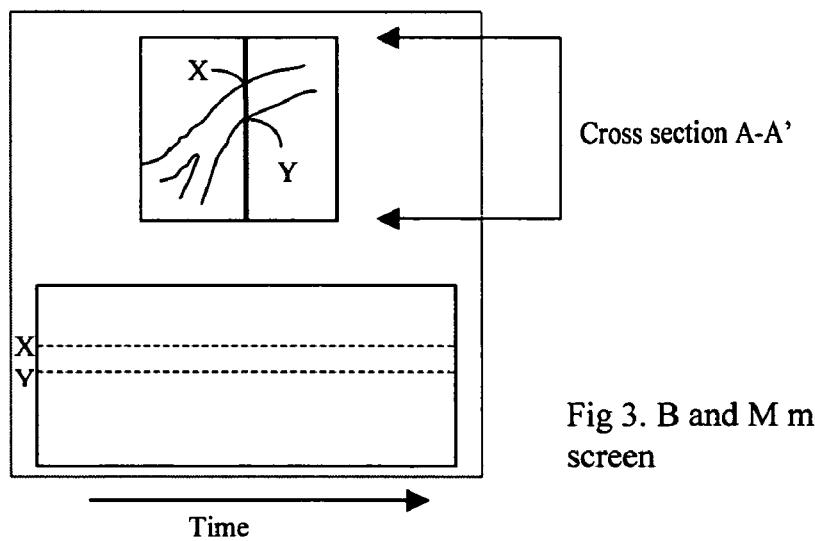
Fig 3. B and M mode on the same screen
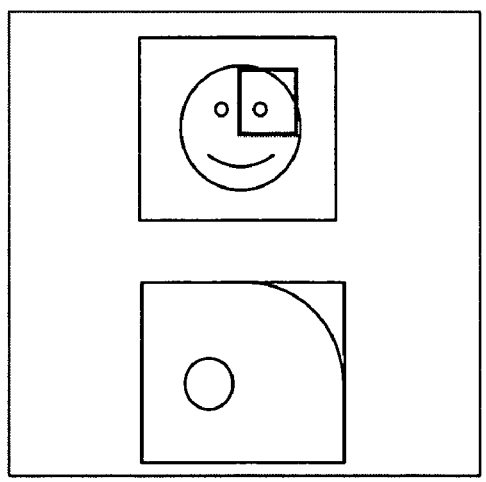
Fig 4. Zoom-out and zoom-in both shown on the screen

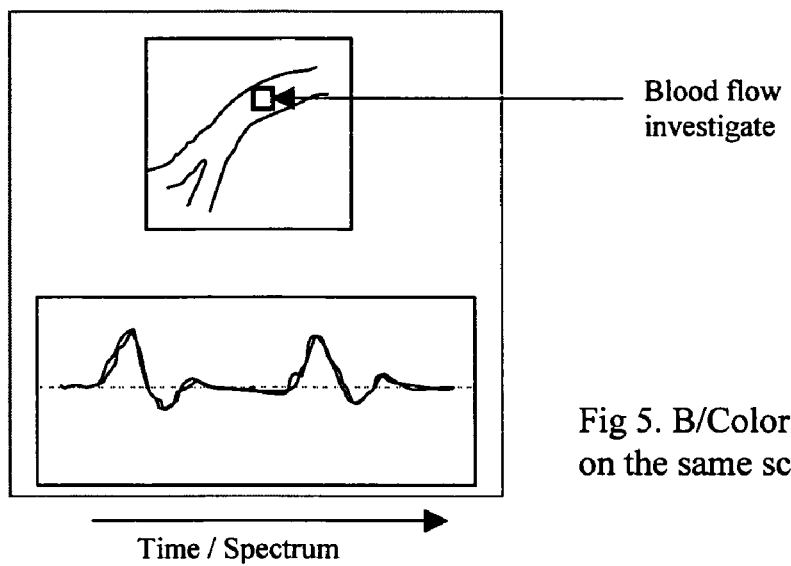
Fig 5. B/Color and Spectral mode on the same screen

USER INTERFACE FOR MEDICAL IMAGING INCLUDING IMPROVED PAN-ZOOM CONTROL

This Application is a Formal Application and claims a Priority Filing Date of Oct. 30, 2004 benefited from a previously filed Application 60/623,616 filed previously by the inventor of this Patent Application.

FIELD OF THE INVENTION

This invention generally relates to system and method for carrying out a medical imaging process. More particularly, this invention relates to an improved imaging display system and method for providing more convenient user control of the pan zoom image display for medical image systems.

BACKGROUND OF THE INVENTION

Even though there are great advancements made in the image display technologies such that scanning images can be displayed with higher resolutions and can be viewed from different angles and zooming in and out at different zooming proportions to perform more accurate diagnoses. However, the user interface for displaying and viewing the medical images are still limited by the requirement to toggle back and forth between the original image and the zoomed images. These toggle back and forth operations are required when a user needs to view zoomed image of different areas of the original image. Such operations generally require an image display user to enter many key stokes. Therefore, it becomes inconvenient for a viewer who needs to view scanned images in different sizes.

In a conventional ultrasound imaging system, there is a dedicated 'Zoom' key in the user interface keyboard to toggle the display in between the original (un-zoomed) image and the zoom-in image. When acquiring a real time ultrasound 2-D image on the screen, the user can press the 'Zoom' key to highlight a graphic boarder called Zoom Region Of Interest (ZROI) for zooming the image, and then use the trackball or arrow key to pan the ZROI on the original un-zoom screen, and press the 'Zoom' key one more time to display the zoom-in image. When the user wants to pan the ZROI to another portion of the display, he/she needs to press the Zoom key again to go back to the original un-zoom image and then pan the zoom box, and press the zoom key again to see the zoom-in image.

For these reasons, a need still exists for those of ordinary skill in the art to provide an improved method and system for medical image display. Specifically, it is desirable to provide an improved user interface to simplify the operations when a user of the image display system needs to magnify different areas in an image. Specifically, it is desirable that the number of key strokes can be reduced by automating toggles of display images between the ZROI zoomed-in display and the "zoomed-out" global images such that a user does not have to enter so many key strokes to change from one mode of viewing and display to another.

SUMMARY OF THE INVENTION

It is an aspect of the present invention to provide a user interface for applying to a medical image viewing system with enhanced image viewing control to reduce the operational steps required by a viewer to switch the zooming of different areas such that the above discussed limitations and difficulties may be resolved.

In another aspect, the present invention provides a medical scan image display system with an anticipatory display-mode switch function that anticipate a viewer's alternative viewing mode for the purpose of reducing the operational steps required to change from one viewing mode to another viewing mode back and forth.

In yet another aspect, the present invention further provides an improved medical image viewing system that provides at least a global viewing mode to view the entire scan image and a zooming mode for viewing a zoomed area on the display system. The improved image view system anticipates that as a user takes certain action through an input device, the user's intend is to switch from one viewing mode to another viewing mode and resume back to the original mode. Therefore, the improved medical image viewing system provides automated viewing mode change functions to reduce the processing steps required by the user to change from one viewing mode to another viewing mode.

In yet another aspect, the present invention provides a method for automatically switch from a viewing mode, e.g. a zoomed image viewing mode, to a global viewing mode once a motion is sensed on a user interface device such as a computer mouse, trackball, key board, or any inputting device. The medical image viewing system therefore anticipates that as a viewer complete viewing a zoomed image on the display screen, the next logic step is most likely to switch back to the global image and to select a different area for another zoomed image inspection.

In yet another aspect, the present invention provides a method for automatically switch from a viewing mode, e.g. a global image viewing mode, to a zoomed viewing mode once a panned area is defined by a viewer through a user interface device such as a computer mouse, trackball, or key board. The medical image viewing system anticipates that as a viewer completes viewing a global image and now confirms a panned area; the next logic step is most likely to switch back to the zoomed image viewing for the panned area as it has completely defined now.

These and other objects and advantages of the present invention will no doubt become obvious to those of ordinary skill in the art after having read the following detailed description of the preferred embodiment, which is illustrated in the various drawing figures.

BRIEF DESCRIPTION OF FIGURES

The present invention is described in detail below with reference to the following Figures.

FIG. 1 is a diagram for showing the two viewing modes of an image display system where a zoomed image display represents an amplified image of a panned area on a global image.

FIGS. 2A to 2G are a series of images showing the automatic switching operations provided by an improved imaged display system of this invention.

FIG. 3 shows images for illustrating different operational sequences of another preferred embodiment of an ultrasonic image scanning system of this invention.

FIG. 4 shows a display system to simultaneously display a zoomed-out image, as the upper image, and a zoomed-in image as the lower image, with different screen layouts.

FIG. 5 shows a display system further switches automatically from a first display mode, e.g., a global B or B/Color image shown as the top image, to a second display mode, e.g., a blood flow spectrum of a specific vessel on the top image as shown on the bottom image.

DESCRIPTION OF PREFERRED EMBODIMENTS

Medical imaging systems are known. For example, ultrasound imaging is discussed in the '080 patent and in U.S. Pat. No. 6,248,071. The disclosures made in that Patent are hereby incorporated by reference in its entirety for all purposes in this Patent Application. As illustrated in FIG. 1, a medical image display system is frequently toggled back and forth between a global view and zoom of an image as shown on the left side of FIG. 1. Then with a panned area, a zoom image is shown with a magnified image of the panned area. The zoomed image as shown on the right hand side of FIG. 1 is often required to carry out detail inspection to determine if any abnormal or unusual characteristics are detected in the scanned image for the purpose of carrying out a diagnosis.

Referring to FIGS. 2A to 2F for the operational sequences of a preferred embodiment. In FIG. 2A, an original image is shown on the screen and in FIG. 2B, a user presses a zoom key to bring out the ZROI graphic and then resize and/or pan the ZROI box with a track ball on a user select area. In FIG. 3C, as soon as the panning action is completed, a zoomed image is shown on the screen, therefore a separate keystroke to show the zoomed image is not required. In FIG. 3D, as soon as the user touches the trackball or the keyboard, an original image is shown automatically. Another sets of keystrokes are therefore not necessary to end the zoom view to switch back to the original global view. In FIG. 3E, the user can again pan the ZROI graphic box to a different area, and then in FIG. 2F, the display switch to a zoomed image when the ZROI window stays at the same location (i.e., if trackball is stationary) for a certain length of time (e.g. 0.3 second) thus saving additional keystrokes that are generally required to switch from a global view to a zoomed view.

Referring to FIG. 3 for different operational sequences of another preferred embodiment of an ultrasonic image scanning system of this invention. The image scanning system includes a display system that simultaneously displays at least two images with a first image as shown in the upper image that displays the tissue and blood vessels, generally referred to as a "B-image with 2-D brightness". The display system further display a second image, e.g., a lower image, that shows a cross sectional view of the organic object cut off at a scrolling line, e.g., line A-A', across the first image, generally referred to as a M-image displayed with motion scrolling mode. In the normal operation, the M-image is updated in real time and the B-image is in frozen state. At the moment the user touch the trackball, the display switches to B-image in real time and M in frozen mode. Now the user can use the trackball to alter the A-A' on the B-image for M-image display. As soon as the trackball stop (>0.3 sec for instance), the display will switch to M-image in real time and B in frozen. Referring to FIG. 4 for another preferred embodiment, wherein the display system further simultaneously displays a zoomed-out image, e.g., the upper image, and a zoomed-in image, e.g., the lower image, with different screen layouts. In normal operation, the Zoom-in image is in real time update and the zoom-out image is in frozen state. When the user touches the trackball and uses it to pan and/or resize the ZROI, the zoom-out image is automatically activated. The zoom-in image resumes to the real time update mode when the trackball stops for less than 0.3 sec for instance.

Referring to FIG. 5 for another preferred embodiment, wherein the display system further switches automatically from a first display mode, e.g., a global B or B/Color image shown as the top image, to a second display mode, e.g., a blood flow spectrum of a specific vessel on the top image as shown on the bottom image. The second display mode, e.g., the image for showing the blood flow spectrum of a specific vessel is to display an image that is graphically unrelated and independent from an image displayed in the first display mode, e.g., the B or B/Color image shown in the global view mode. In the normal display, the Spectrum mode is in real time updating and the B or B/color is in frozen mode. When user touches the trackball and selects different vessel for Spectrum display, the system automatically make B or B/color in real time update mode. As soon as the trackball stops for less than 0.3 sec (for instance), the system switches the Spectrum mode in real time, and B or B/color in frozen.

Among some embodiments of the present invention are a system and a method capable of performing ultrasound or different method of scanning and to display these images on a viewing screen. Among some embodiments of the present invention are a 3-dimensional Computer Aided Diagnostic (CAD) software package that can further enhance the analyses and display of the scanned images. In a different embodiment, the auto pan zoom function can be applied to ultrasound B mode (including Tissue Harmonic B), and simultaneous B/Color flow mode Embodiments of this invention further include display system with image sources obtained from medical scanning operations for diagnostic inspections and such image display systems includes various user interfaces with devices and software tools to control the display in different angles, different amplified proportions and different colors for better viewing and more accurate diagnoses.

Embodiments of the present invention include implementations of software and hardware systems and functions for providing a user interface for medical imaging. Embodiments of the present invention also include a medical imaging method and a medical imaging system that include method and system for providing the improved user interface.

Embodiments of the present invention further include medical scanning systems connecting to image display systems with options for either real time display or post scanning display. One exemplary system is an ultrasound scanning system connected to an image display system with user graphic interface and user controller to change display images for viewing at different viewing modes.

In one embodiment, the controller may include a computer system, for example, a special-purpose or general-purpose computer that is programmed with software according to an embodiment of the present invention. The software may reside on a computer memory device from which the software can be read to ultimately instruct a computer system to perform steps. Any type of computer memory device may be used, for nonexclusive example, ROM, RAM, optical media, magnetic media, physical media, and the like. Media may be of any competent form, for example, disk, tape, stick, integrated circuit, and the like. Computer systems are well known, and any competent type may be used, for example, general-purpose, or special-purpose, or embedded, or physically or wirelessly networked, or multi-processor, or single-processor, and so forth. Any competent operating system may be used, for example, Microsoft Windows, Unix, GNU (e.g., GNU/Linux), or any other competent operating system whatsoever.

In another embodiment, the controller is configured to be able to communicate at least occasionally with various portions of the remainder of the medical imaging system, e.g., via a connector or bus or network or the like, e.g., via wires or wirelessly, according to any competent command structure or communication/interconnection protocols and any operable and properly functional protocols that may or may not be commercially available.

In another embodiment, the controller operates to produce information for display to a user and to accept input from the user. The displaying and inputting may be at close physical proximity to the controller's main computer processor, or the displaying and inputting may be via a client computer or terminal at a remote location. For example, the controller may be an Internet or intranet or other type of server, and the user may interact remotely with the controller from a browser or other remote interface.

In another embodiment, there is a controller, or a method thereof, or a computer-readable memory product that includes the software thereof, that provides a user interface that includes an improved Pan-Zoom control that requires fewer keystrokes to operate than is required under the conventional approach. Remaining portions of the controller (or its method or software) can be according to any conventional system or method.

In a specific embodiment, the present invention provides an automatic Pan-Zoom for user interface in any ultrasound system so the user can reduce the keystrokes in operating the unit. According to some embodiments, the user can easily manipulate the pan zoom window with trackball (or mouse, or joystick, or touchpad, or cursor keys, or the like) and know the portion of the full image corresponds to the zoom window. Once the user touches the trackball (or any inputting device . . . ) in the zoom-mode during real-time scanning, the screen will automatically switch back to the original un-zoomed image with a ZROI graphic box highlighted, once the ZROI is panned and stay at the same location for a certain time (e.g. 0.3 second) (e.g., a parameter within a range of about 0.2 to 1.0), the system will automatically go back to the magnified zoom-in display, and the user does not have to hit the zoom mode key to toggle back and forth between the zoom and un-zoomed modes. This makes it easy for the user to operate the unit and increase the throughput rate.

In a specific embodiment, the controller (or its method or software) may have a soft-menu to allow the user to set the system default to either the conventional pan zoom or the auto image control Pan zoom.

In a specific embodiment, the auto pan zoom function can be applied to ultrasound B mode (including Tissue Harmonics B), and simultaneous B/Color flow mode. The auto zoom function has options and can be applied to the rectangular and trapezoid image for flat linear array probe, or sector image for the curve linear array and phase array probe. The implementation of the zoom function can be in read zoom, which the zoom image is interpolated from the acquired image in the memory; or the write zoom, which the zoom image is a new acquisition data with different resolution setting.

In a specific embodiment, the auto pan zoom can be applied to the offline ultrasound image reviewing station, in which the plural of images are display on the screen as slides, and the highlighted slide image is magnified to the center of the display. There may be slides behind the center of the display and are block by the magnified image. When the user access to the trackball or any inputting device, the screen will go back to the original display with all slides on the screen, and the magnified zoom image at the center disappear. Once the trackball stay at the same slide for a moment of time, the display will automatically be back to the highlighted image zoom at the center of the screen. The display can stay at 'all slides' image if the trackball cursor is not within any slide boarder.

With this auto pan zoom function, a soft-menu can be used to set up the dwelling time for the trackball in order for the system to decide if it needs to resume to the zoom image screen. For some embodiments of the present invention, the image display systems are especially useful for implementations in which the zoom-mode image window fills the entire physical display screen or in which the zoom-mode image window is the only medical image window on the physical display screen.

In another preferred embodiment, the implementation of the zoom function can be in read zoom, which the zoom image is interpolated from the acquired image in the memory; or the write zoom, which the zoom image is a new acquisition data with different resolution setting. Furthermore, the auto pan zoom operational processes can also be applied to the offline ultrasound image reviewing, in which the plural of images are display on the screen as slides, and the highlighted slide image is magnified to the center of the display. There may be slides behind the center of the display and are block by the magnified image. When the user access to the trackball, the screen will go back to the original display with all slides on the screen, and the magnified zoom image at the center disappear. Once the trackball stay at the same location for a moment of time, the display will automatically be back to the highlighted image zoom at the center of the screen.

The description and the drawings of the present document describe examples of embodiment(s) of the present invention and also describe some exemplary optional feature(s) and/or alternative embodiment(s). It will be understood that the embodiments described are for the purpose of illustration and are not intended to limit the invention specifically to those embodiments. Rather, the invention is intended to cover all that is included within the spirit and scope of the invention, including alternatives, variations, modifications, equivalents, and the like.

I claim:

1. An ultrasonic image scanning system for scanning an organic object comprising:
   a controller;
   a display system for displaying a scanned image of said organic object in a plurality of display modes, wherein the display system is configured to simultaneously display the scanned image in real-time in a first active display mode and frozen-state in a second active display mode; and
   a user input device sensor configured to sense a touch and, in response to the touch, automatically switching the first active display mode from real-time to frozen-state and the second active display mode from frozen-state to real-time,
   wherein the display system is connected to the controller, wherein the user input device sensor is connected to the controller, wherein the controller is configured to count a length of time said user input device stays idle in one of the active display modes, and wherein the controller is configured to automatically switch said one of the active display modes back to a last active display mode when the length of time reaches a predefined idle time limit.

2. The ultrasonic image scanning system of claim 1 wherein said display system further simultaneously displays at least two images with a first image showing an external view of said organic object and a second image showing a cross sectional view of said organic object cut off at a scrolling line across said first image wherein said second image is further activated to show a cross sectional view corresponding to a cross section as said scrolling line move to different positions over said first image.

3. The ultrasonic image scanning system of claim 1 wherein said display system further simultaneously displays a zoomed-in image of the scanned object and a zoomed-out image of the scanned object with different screen layouts.

4. The ultrasonic image scanning system of claim 1 wherein said controller is configured to switch automatically from the first active display mode of the plurality of display modes to the second active display mode of the plurality of display modes, wherein said second active display mode is for displaying an image that is graphically unrelated and independent from an image displayed in said first active display mode.

5. The ultrasonic image scanning system of claim 1 wherein the controller is configured such that an operator can set said predefined idle time limit for automatically switching from one of said display modes to another one of said display modes.

6. The ultrasonic image scanning system of claim 1 further comprising: a three dimensional (3-D) image as a first scan mode of the plurality of display modes and B or B/color as a second scan mode of the plurality of display modes.

7. The ultrasonic image scanning system of claim 1 further comprising: a Spectral Doppler as a first scan mode of the plurality of display modes and B or B/color as a second scan mode of the plurality of display modes.

8. The ultrasonic image scanning system of claim 1 further comprising: a M-mode as a first scan mode of the plurality of display modes and B or B/color as a second scan mode of the plurality of display modes.

9. The ultrasonic image scanning system of claim 1 further comprising: a Zoom-out as a first scan mode of the plurality of display modes and Zoom-in as a second scan mode of the plurality of display modes.

10. The ultrasonic image scanning system of claim 1 wherein said controller comprises an automatic pan zoom function for application to an ultrasound B mode and a simultaneous B/color flow mode.

11. The ultrasonic image scanning system of claim 1 further comprising: an image source for interfacing and obtaining a display image from different image scanning systems.

12. The ultrasonic image scanning system of claim 1 wherein said controller includes a color flow imaging management function to manage a display of images in different color modes.

13. The ultrasonic image scanning system of claim 1 wherein: said controller includes a display management software package to manage a display of images in different angles, amplified proportions and different user interfaces.

14. An image display system for displaying an ultrasound image of an organic object in different display modes comprising:
a controller,
a display connected to the controller and configured to display the ultrasound image in a plurality of display modes, wherein the display is configured to simultaneously displaying the ultrasound image in real-time in a first active display mode and frozen-state in a second active display mode; and
a user input device sensor connected to the controller and configured to sense a touch and, in response to the touch, automatically switching the first active display mode from real-time to frozen-state and the second active display mode from frozen-state to real-time;
wherein the first and second active display modes are selected from the group consisting of (a) a three dimensional (3-D) image and B or B/color, (b) a Spectral Doppler and B or B/color, (c) a M-mode and B or B/color, and (d) a Zoom-out and Zoom-in;
wherein the controller counts a length of time said user input device is idle in at least one of said plurality of display modes and automatically switches said display mode back to a last display mode at a predefined idle time limit.

15. The image display system of claim 14 wherein said display system further enabling an operator to set said predefined idle time limit for automatically switching from said display mode to said last display mode when said user input device stays idle.

16. The image display system of claim 14 wherein said user input device sensor sensing the motion of a user input device sensor in a zoomed view display mode causes the controller to automatically switch from said zoomed view display mode to a global view display mode.

17. The image display scanning system of claim 14 wherein said controller counts a length of time said user input device sensor stays idle in a global view display mode before switching back to a zoomed view display mode.

18. A method for displaying an ultrasonic image in different display modes comprising:
simultaneously displaying the ultrasonic image in real-time in a first active display mode and frozen-state in a second active display mode;
sensing a touch of a user input device,
in response to the touch, automatically switching the first active display mode from real-time to frozen-state and the second active display mode from frozen-state to real-time;
using a controller, counting a length of time said user input device is idle in at least one of said active display modes, and
automatically switching said display mode back to a last display mode when the length of time reaches a predefined idle time limit.

19. The method of claim 18 further comprising: enabling an operator to set said predefined idle time limit for automatically switching from said display mode to said last display mode when said user input device stays idle.

20. The method of claim 18 wherein said step of sensing a motion of a user input device is a step of sensing said motion of said user input device in a zoomed view display mode and wherein the first active display mode is a zoomed view display mode and the second active display mode is a global view display mode.

21. The method of claim 18 wherein said step of counting comprises counting said length of time when said user input device stays idle in a global view display mode.

22. The method of claim 18 further comprising: implementing a display control software package to manage a display of images in different angles, amplified proportions and different user interfaces.

* * * * *